(12) United States Patent
Fujita et al.

(10) Patent No.: US 10,987,374 B2
(45) Date of Patent: Apr. 27, 2021

(54) COMPOSITION FOR PROMOTING PRODUCTION OF IMMUNOSTIMULATORY FACTOR

(71) Applicant: Kyoto University, Kyoto (JP)

(72) Inventors: Takashi Fujita, Kyoto (JP); Hiroki Kato, Kyoto (JP); Tetsuya Nakazaki, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 16/322,626

(22) PCT Filed: Jul. 31, 2017

(86) PCT No.: PCT/JP2017/027638
§ 371 (c)(1),
(2) Date: Jun. 4, 2019

(87) PCT Pub. No.: WO2018/025793
PCT Pub. Date: Feb. 8, 2018

(65) Prior Publication Data
US 2019/0290674 A1    Sep. 26, 2019

(30) Foreign Application Priority Data

Aug. 2, 2016  (JP) .............................. JP2016-151836
Feb. 8, 2017  (JP) .............................. JP2017-021008

(51) Int. Cl.
| A61K 39/12 | (2006.01) |
| A61K 31/713 | (2006.01) |
| A23L 33/13 | (2016.01) |
| A61K 9/00 | (2006.01) |
| A61K 35/76 | (2015.01) |
| A61K 36/48 | (2006.01) |
| A61K 36/81 | (2006.01) |
| A61K 36/899 | (2006.01) |

(Continued)

(52) U.S. Cl.
CPC ............ *A61K 31/713* (2013.01); *A23L 33/13* (2016.08); *A61K 9/0073* (2013.01); *A61K 35/76* (2013.01); *A61K 36/48* (2013.01); *A61K 36/81* (2013.01); *A61K 36/899* (2013.01); *A61K 39/39* (2013.01); *A61P 31/12* (2018.01); *A61P 31/14* (2018.01); *A61P 35/00* (2018.01); *A61P 37/04* (2018.01); *Y02A 50/30* (2018.01)

(58) Field of Classification Search
None
See application file for complete search history.

(56) References Cited

U.S. PATENT DOCUMENTS 9,090,650 B2   7/2015  Seya et al.
2013/0178611 A1  7/2013  Seya et al.

FOREIGN PATENT DOCUMENTS

WO        2012014945 A1    2/2012

OTHER PUBLICATIONS

Valverde et al., "Identification of Oryza saliva endomavirus in rice genotypes from breeding programmes in the United States," Plant Breeding 130(2):271-274 (2011).

(Continued)

*Primary Examiner* — M Franco G Salvoza
(74) *Attorney, Agent, or Firm* — McNeill Baur PLLC

(57) ABSTRACT

According to the present invention, various diseases, such as viral diseases, cancer, and multiple sclerosis, can be prevented and improved by using an immunostimulatory factor production-promoting composition comprising genomic double-stranded RNA of a plant-derived endornavirus.

14 Claims, 11 Drawing Sheets

(51) Int. Cl.
*A61K 39/39* (2006.01)
*A61P 31/14* (2006.01)
*A61P 37/04* (2006.01)
*A61P 31/12* (2006.01)
*A61P 35/00* (2006.01)

(56) References Cited

OTHER PUBLICATIONS

Supplementary European Search Report issued in EP patent application No. 17836898.1, dated Dec. 19, 2019, 7 pages.
International Search Report issued in PCT/JP2017/027638, dated Oct. 3, 2017, 5 pages.

COMPOSITION FOR PROMOTING PRODUCTION OF IMMUNOSTIMULATORY FACTOR

TECHNICAL FIELD

The present invention relates to an immunostimulatory factor production-promoting composition.

BACKGROUND ART

No effective therapy has been established for general viral diseases. In general, therapy corresponding to each viral disease is used. For example, interferon therapy is used for hepatitis C etc., and administration of antiviral drugs (Tamiflu, Relenza, etc.) is used for specific viral diseases, such as influenza. However, because of the risk of side effects, cost, etc., it is difficult to continuously apply interferon for prophylactic purposes. Moreover, current antiviral drugs generally comprise synthetic low-molecular-weight compounds as active ingredients, and it is also difficult to continuously use them for prophylaxis, because of cost etc.

For cancer, pharmacotherapy is performed, such as anti-cancer drug therapy, which is intended to act on DNA synthesis etc. to suppress the growth of cancer cells, and interferon therapy, which is intended to activate immunity to suppress the growth of cancer cells. However, because of the risk of side effects, cost, etc., it is difficult to continuously use interferon for the purpose of prophylaxis. Moreover, current anti-cancer drugs generally comprise synthetic low-molecular-weight compounds, antibodies, etc., as active ingredients, and it is also difficult to continuously use them for the purpose of prophylaxis, in terms of cost etc.

Multiple sclerosis is also treated with, for example, low-molecular-weight compounds and interferon, as with viral diseases, cancer, etc.; however, it is difficult to continuously use them for the purpose of prophylaxis, because of the risk of side effects, cost, etc.

Thus, there is no known therapy that can be widely applied to various diseases, such as viral diseases, cancer, and multiple sclerosis, and that can also be used for prophylaxis of these diseases (i.e., low risk of side effects and low cost).

It is reported that endornaviruses are present in plants, particularly green peppers, rice, and like edible plants that are eaten daily (NPL 1, NPL 2, etc.). Some types of RNA viruses are considered to induce interferon production through signal-transduction pathways via MDAS, RIG-I, etc., consequently leading to in vivo immunostimulation. However, the association between endornaviruses and viral diseases is not known.

CITATION LIST

Non-Patent Literature

NPL 1: Journal of General Virology (2011), 92, 2664-2673.
NPL 2: Journal of General Virology (2011), 92, 2674-2678.

SUMMARY OF INVENTION

Technical Problem

An object of the present invention is to provide a method for preventing and improving various diseases, such as viral diseases, cancer, and multiple sclerosis.

Solution to Problem

The present inventors conducted extensive studies in light of the above problems, and consequently found that genomic double-stranded RNA of plant-derived endornaviruses is effective to promote the production of immunostimulatory factors, such as interferon. Further, the present inventors also found that a wide range of diseases, such as viral diseases, cancer, and multiple sclerosis, can be prevented and improved by this double-stranded RNA. As a result of pursuing further studies based on these findings, the present inventors have completed the present invention.

Specifically, the present invention includes the following embodiments:

Item 1. An immunostimulatory factor production-promoting composition, comprising genomic double-stranded RNA of a plant-derived endornavirus.

Item 2. The immunostimulatory factor production-promoting composition according to Item 1, wherein the plant is a *Capsicum* plant, a rice plant, or a *Vicia* plant.

Item 3. The immunostimulatory factor production-promoting composition according to Item 1 or 2, wherein the genomic double-stranded RNA has a length of 8 to 20 kbp.

Item 4. The immunostimulatory factor production-promoting composition according to any one of Items 1 to 3, wherein the genomic double-stranded RNA is linear.

Item 5. The immunostimulatory factor production-promoting composition according to any one of Items 1 to 4, which is a pharmaceutical composition.

Item 6. The immunostimulatory factor production-promoting composition according to any one of Items 1 to 5, which is an intranasal preparation.

Item 7. The immunostimulatory factor production-promoting composition according to any one of Items 1 to 5, which is an oral preparation.

Item 8. The immunostimulatory factor production-promoting composition according to any one of Items 1 to 4, which is a food composition.

Item 9. The immunostimulatory factor production-promoting composition according to any one of Items 1 to 8, which is used as an immunostimulatory composition.

Item 10. The immunostimulatory factor production-promoting composition according to any one of Items 1 to 8, which is used as an antiviral composition.

Item 11. The immunostimulatory factor production-promoting composition according to Item 10, wherein the virus is an RNA virus.

Item 12. The immunostimulatory factor production-promoting composition according to any one of Items 1 to 5, which is used as an adjuvant.

Item 13. The immunostimulatory factor production-promoting composition according to any one of Items 1 to 8, which is used as a composition for preventing or improving cancer.

The present invention also includes the following embodiments:

Item 14. An immunostimulatory factor production-promoting method, comprising applying genomic double-stranded RNA of a plant-derived endornavirus to an animal or a human.

Item 15. Genomic double-stranded RNA of a plant-derived endornavirus for promoting immunostimulatory factor production. Item 16. Use of genomic double-stranded RNA of a plant-derived endornavirus for producing an immunostimulatory factor production-promoting composition.

Item 17. Use of genomic double-stranded RNA of a plant-derived endornavirus for promoting immunostimulatory factor production.

Advantageous Effects of Invention

According to the present invention, the production of immunostimulatory factors, such as interferon, can be promoted by using genomic double-stranded RNA of plant-derived endornaviruses, and the immunity of the body can be thereby activated. Therefore, the genomic double-stranded RNA of plant-derived endornaviruses can be used for various applications (e.g., for prevention and improvement of viral diseases, cancer, multiple sclerosis, etc.; and as adjuvants), based on its immunostimulatory factor production-promoting action and immunostimulatory action. Moreover, for antivirus use, the genomic double-stranded RNA of plant-derived endornaviruses can be applied to various types of viruses.

Furthermore, the genomic double-stranded RNA of plant-derived endornaviruses is a component contained in plants (in particular, edible plants), and is thus considered to be highly safe. Moreover, according to the present invention, the double-stranded RNA can be efficiently purified from plants. Accordingly, the genomic double-stranded RNA of plant-derived endornaviruses can be used more safely at lower cost, and is suitable for continuous use for the purpose of preventing diseases, such as viral diseases, cancer, and multiple sclerosis.

DESCRIPTION OF EMBODIMENTS

Figure 1:
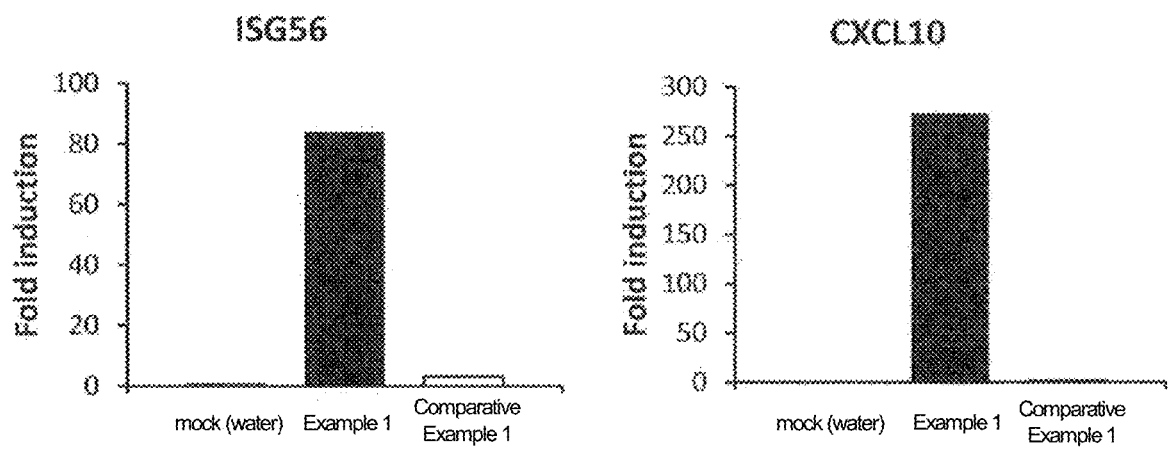
FIG. 1 shows the results of the in vitro immunostimulatory factor production test 1 of Example 2. The vertical axis represents relative expression levels.

In the present specification, the terms "comprise" and "contain" include the concepts of "comprise," "contain," "essentially consist of," and "consist of."

In one embodiment, the present invention relates to an immunostimulatory factor production-promoting composition comprising genomic double-stranded RNA of a plant-derived endornavirus (also referred to as "the composition of the present invention" in the present specification). This is described below.

1. Genomic Double-Stranded RNA of Plant-Derived Endornavirus

The "genomic double-stranded RNA of a plant-derived endornavirus," which is an active ingredient of the composition of the present invention, is described below.

The genomic double-stranded RNA of a plant-derived endornavirus is not limited, as long as it is genomic double-stranded RNA of an endornavirus contained in a plant.

Various plants containing endornaviruses are known. Examples of such plants include *Capsicum* plants, such as *Capsicum annuum* (red pepper), *Capsicum frutescens* (*Frutescens* pepper), *Capsicum baccatum* (Aji Amarillo), and *Capsicum chinense* (Habanero chili pepper); rice plants, such as *Oryza sativa* (e.g., Koshihikari cultivar); *Vicia* plants; and the like. Examples of cultivars of *Capsicum annuum* containing endornaviruses include California Wonder, Yolo Wonder, Kyousuzu, Kyounami, Kyoumidori, Ace, Suigyokunigou, High Green, Jumbo Colour, Marengo, Avelar, Casca Dura, King Arthur, VR-4, Magda, Bonnie's Green Bell, Red Bell, Chocolate Beauty Sweet, Pimento Sweet, Cayenne Long Red Thick, Super Cayenne, and the like. Examples of cultivars of *Capsicum frutescens* containing endornaviruses include Greenleaf, LSU, PI 159239, PI 193470, and the like. Examples of cultivars of *Capsicum baccatum* containing endornaviruses include Monk's Hat, PI 238061, PI 633752, PI 260549, PI 215699, PI 260590, PI 260543, PI 441589, PI 257135, PI 337524, PI 337522, C00754 (AVRDC), 001218 (AVRDC), C01527 (AVRDC), C01300 (AVRDC), and the like. Examples of cultivars of *Capsicum chinense* containing endornaviruses include PI 159236, PI 315008, PI 315023, PI 315024, PI 273426, C00943 (AVRDC), C00949 (AVRDC), and the like.

Endornaviruses contained in plants are generally not covered with capsid, and are composed of double-stranded RNA, which is a genome. In the present invention, this double-stranded RNA is used as an active ingredient.

The genomic double-stranded RNA used as an active ingredient in the present invention may be the full-length genome of an endornavirus, or may be a fragment thereof. However, from the viewpoint that immunostimulatory factor production-promoting action can be more efficiently exhibited, the length of the genomic double-stranded RNA is desirably longer, and is, for example, 8 to 20 kbp, preferably 10 to 18 kbp, and more preferably 12 to 16 kbp.

The genomic double-stranded RNA used as an active ingredient in the present invention generally has a linear shape, although it is not limited thereto.

The sequence of the genomic double-stranded RNA used as an active ingredient in the present invention is not limited. In the present invention, it has been found that endornavirus genomic double-stranded RNAs purified from two different plants, i.e., genomic double-stranded RNAs with different sequences, have immunostimulatory factor production-promoting action. Accordingly, this immunostimulatory factor production-promoting effect is considered to be independent of the sequence of the genomic double-stranded RNA of a plant-derived endornavirus.

2. Production Method

The method for producing the "genomic double-stranded RNA of a plant-derived endornavirus," which is an active ingredient of the composition of the present invention, is described below.

The "genomic double-stranded RNA of a plant-derived endornavirus," which is an active ingredient of the composition of the present invention, can be obtained by a method comprising purifying nucleic acids (in particular, RNA) from plant cells containing endornaviruses. For example, purification can be performed by suitably combining a cell lysis step, a deproteinization step, a nucleic acid concentration step, a nucleic acid solubilization step, etc.

The plant cells as the material are not limited, as long as they are plant cells containing endornaviruses. In terms of safety, the plant cells are preferably edible plant cells, and more preferably cells of edible parts (e.g., fruits, seeds, or parts thereof) of edible plants. Moreover, from the viewpoint that desired products can be obtained at lower cost, it is desirable to use, of edible parts, cells of generally discarded parts (e.g., bran of rice seed (rice)).

The cell lysis step is not limited, as long as the cell membrane of the plant cells can be broken. Various known methods can be used. For example, a step of mixing with a solution containing a surfactant can be used. The surfactant is not limited, and various surfactants can be used; however, preferable surfactants have strength to a degree that does not break nuclear membrane. This can prevent contamination of the cells with genomic DNA, and purer endornavirus genomic double-stranded RNA can be obtained. Preferable examples of such surfactants include sodium deoxycholate. The concentration of the surfactant is suitably adjusted depending on the type thereof. For example, in the case of sodium deoxycholate, the concentration thereof is, for example, about 0.2 to 1%, and preferably about 0.3 to 0.7%. Moreover, in the case of method 4, described later, the concentration is preferably about 0.15 to 0.35%. After mixing, it is desirable to remove insoluble components by centrifugal separation or the like.

The deproteinization step is not limited, as long as proteins can be insolubilized. Various known methods can be used. For example, a step of mixing with organic solvents, such as phenol, chloroform, and a mixed solvent containing phenol and chloroform, can be used. After mixing, insolubilized proteins are generally removed by centrifugal separation or the like. The deproteinization step may be performed several times (e.g., 2 to 4 times), if necessary.

The nucleic acid concentration step is not limited, as long as the nucleic acid can be precipitated by centrifugal separation or the like. Various known methods can be used. For example, alcohol precipitation, salting out, or the like can be used. Alcohols used for alcohol precipitation are not limited. Examples include ethanol, isopropanol, polyethylene glycol, and the like. Examples of salts used for salting out include lithium chloride, sodium chloride, ammonium acetate, sodium acetate, and the like; and preferably lithium chloride. The nucleic acid concentration step may be performed several times (e.g., 2 or 3 times), if necessary, by combining alcohol precipitation and salting out.

The nucleic acid solubilization step is not limited, as long as the nucleic acid (in particular, double-stranded RNA) contained in the precipitate obtained in the nucleic acid concentration step can be solubilized. Various known methods can be used. For example, a step of suspending the precipitate obtained in the nucleic acid concentration step in a solution containing a chelating agent can be used. Examples of chelating agents include sodium citrate, trisodium hydrogen ethylenediaminetetraacetate, and the like.

In addition to the above steps, other steps, such as a cleaning step (e.g., rinsing with an aqueous ethanol solution, etc.) and a further purification step (e.g., various types of chromatography, such as gel filtration), may be combined, if necessary.

Specific methods for obtaining the "genomic double-stranded RNA of a plant-derived endornavirus," which is an active ingredient of the composition of the present invention, include a method that sequentially performs the deproteinization step and alcohol precipitation (method 1); a method that sequentially performs the cell lysis step, the deproteinization step, alcohol precipitation, and salting out (method 2); a method that sequentially performs the cell lysis step, alcohol precipitation (preferably polyethylene glycol precipitation), salting out, the deproteinization step, and alcohol precipitation (method 3); a method that sequentially performs the cell lysis step, alcohol precipitation, the nucleic acid solubilization step, and alcohol precipitation (method 4); and the like.

Among these, method 3 is suitable for larger-scale production, because the amount of the solution can be reduced by the first alcohol precipitation, and the amount of the organic solvent used in the deproteinization step can thereby be reduced as well.

Moreover, method 4 makes it possible to obtain endornavirus genomic double-stranded RNA as a viscous pasty precipitate. This precipitate is formed into a powder shape by freeze drying or the like, whereby the double-stranded RNA can be stored for a long period of time. In method 4, it is preferable that, of the two alcohol precipitations, the alcohol concentration in the first alcohol precipitation is set lower (e.g., the alcohol concentration is set to 10 to 30%, and preferably 15 to 25%), and that the alcohol concentration in the second alcohol precipitation is set higher (e.g., the alcohol concentration is set to 50 to 80%, preferably 60 to 75%, and more preferably 60 to 70%).

3. Use

The use of the composition of the present invention is described below. In the following, when the composition of the present invention is used as a pharmaceutical composition, the term "improvement" can be read as "treatment."

The genomic double-stranded RNA of a plant-derived endornavirus has immunostimulatory factor production-promoting action, and thus can be used for various compositions for promoting the production of immunostimulatory factors (pharmaceutical compositions, food compositions, oral compositions, etc.). The genomic double-stranded RNA of a plant-derived endornavirus can be formed into various compositions directly or together with common components, and can be applied to animals and humans (for example, by administration, ingestion, inoculation, etc.).

The composition of the present invention can promote the production of immunostimulatory factors, such as interferon (e.g., IFN-β1 and IFNα4), interferon-stimulated factors (e.g., ISG56, BST2, IFITM3, CXCL1, CXCL2, and Pai-1), cytokines (e.g., IL6, and INFα), and interferon-induced genes (e.g., Cxcl10). The composition of the present invention can thereby activate the body's immunity. Therefore, the composition of the present invention can be used as an immunostimulatory composition.

The composition of the present invention can also be used as an antiviral composition (a composition for preventing or improving viral infections). This is considered to be based on the above actions (immunostimulatory factor production-promoting action and immunostimulatory action) of the composition of the present invention. Accordingly, the composition of the present invention is considered to exhibit antiviral action on various viruses, regardless of the type of virus.

The target virus is not limited. Examples include influenza viruses (e.g., type A and type B), rubella virus, Ebola virus, coronavirus, measles virus, varicella zoster virus, herpesvirus, mumps virus, arbovirus, enterovirus, adenovirus, RS virus, norovirus, Human papilloma virus, coxsackie virus, human parvovirus, encephalomyocarditis virus, poliovirus, SARS virus, hepatitis viruses (e.g., hepatitis A virus, hepatitis B virus, hepatitis C virus, hepatitis D virus, and hepatitis E virus), yellow fever virus, rabies virus, hantavirus, dengue virus, Nipah virus, B virus, lyssavirus, rhinovirus, and the like. Among these, RNA viruses, such as influenza virus and encephalomyocarditis virus, are preferable.

The composition of the present invention can also be used as an adjuvant, because it has immunostimulatory factor production-promoting action and immunostimulatory action.

The composition of the present invention can also be used for prevention or improvement of various diseases, such as multiple sclerosis (MS) and cancer, because it has immunostimulatory factor production-promoting action and immunostimulatory action.

The cancer to be prevented or improved is not limited. Examples include skin cancer, multiple myeloma, lung cancer, gastric cancer, liver cancer, esophageal cancer, pancreatic cancer, colorectal cancer, colon cancer, rectal cancer, biliary tract cancer, renal cancer, bladder cancer, cervix cancer, endometrium cancer, ovarian cancer, breast cancer, prostatic cancer, testicular cancer, leukemia, bone tumors, bone cancer, soft tissue tumors, malignant lymphomas, pharyngeal cancer, head and neck cancer, childhood cancer, and the like.

The form of the composition of the present invention is not limited, and forms generally used for each use can be used, depending on the use of the composition of the present invention.

For use as pharmaceutical compositions, health builders, nutritious supplements (e.g., supplements), etc., examples of their forms include dosage forms suitable for oral administration (oral preparations), such as tablets (including orally disintegrating tablets, chewable tablets, foaming tablets, troches, jelly drops, etc.), pills, granules, subtle granules, powders, hard capsules, soft capsules, dry syrups, liquids (including drinkable preparations, suspensions, and syrups), and jellies; and dosage forms suitable for parenteral administration (parenteral preparations), such as nasal drops, inhalants, rectal suppositories, intercalating agents, clysters, jellies, injections, patches, lotions, and creams. Of the parenteral preparations, nasal preparations are preferable.

For use as food compositions, examples of their forms include liquid, gel, or solid foods, such as juices, soft drinks, teas, soups, soybean milk, salad oils, dressings, yoghurts, jellies, puddings, Furikake (dry Japanese seasoning), nursing powdered milk, cake mixes, powders or liquid dairy products, bread, and cookies.

For use as oral compositions, examples of their forms include liquids (solutions, emulsions, suspensions, etc.), semi-solids (gels, creams, pastes, etc.), solids (tablets, granules, capsules, film agents, kneaded materials, molten solids, wax-like solids, elastic solids, etc.), and like any forms. Specific examples include dentifrices (toothpastes, liquid dentifrices, liquid tooth-brushing, powder dentifrices, etc.), mouth washes, ointments, patches, mouth deodorants, foods (e.g., chewing gum, tablets, candies, gummy candies, films, and troches) and the like.

The composition of the present invention may further contain other components, if necessary. The other components are not limited, as long as they can be mixed with pharmaceutical compositions, food compositions, oral compositions, etc. Examples include bases, carriers, solvents, dispersants, emulsifiers, buffers, stabilizers, excipients, binders, disintegrators, lubricants, thickeners, moisturizers, coloring agents, flavoring agents, chelating agents, and the like.

The content of the active ingredient in the composition of the present invention varies depending on the use, usage mode, application object, the state of the applied object, etc., and is not limited. For example, the content of the active ingredient is 0.0001 to 95 wt. %, and preferably 0.001 to 50 wt. %.

The amount of application (e.g., administration, ingestion, or inoculation) of the composition of the present invention is not limited, as long as it is an effective amount for expressing drug effects. In the case of oral administration, the weight of the compound of the present invention as an active ingredient is generally 0.1 to 1000 mg/kg body weight per day, and preferably 0.5 to 50 mg/kg body weight per day. In the case of parenteral administration, the weight of the compound of the present invention is 0.01 to 100 mg/kg body weight, and preferably 0.1 to 10 mg/kg body weight, per day. The above dose is preferably administered once a day, or 2 or 3 times a day, and can be suitably increased or decreased according to the age, pathological conditions, and symptoms.

EXAMPLES

The present invention is described in detail below based on Examples; however, the present invention is not limited to these Examples.

Example 1: Total RNA Purified from Green Pepper (*Capsicum annuum* L. 'grossum,' Kyosuzu)

Total RNA was purified from a green pepper (cultivar name: Kyosuzu), for which it was known that the cells thereof contain endornavirus genomic double-stranded RNA. The specific operation was as follows.

Kyosuzu (green pepper cultivar) was ground with a compression squeezing low-speed juicer ("Iki Iki Kouso-Kun," produced by Odeo Corporation) and centrifuged at 2,000 rpm, and the supernatant was removed. RNase-free water was added until the obtained precipitate was completely dissolved. To the resultant, an equivalent amount of phenol/chloroform solution (TE saturated phenol:chloroform=1:1) was added and vigorously stirred. Then, the mixture was centrifuged (4° C., 2,380 g (centrifugal force), 15 minutes), and the supernatant was collected. After a salt water solution and a double amount of 100% ethanol were added and mixed with 1/10 of the amount of the obtained supernatant, the resultant was allowed to stand at −80° C. for 15 minutes. After centrifugation (4° C., 2,380 g (centrifugal force), 15 minutes) and supernatant removal, the precipitate was washed with 70% aqueous ethanol solution. The remaining solvent was removed by drying under reduced pressure, thereby obtaining total RNA. The total RNA was dissolved in RNase-free water so that the concentration of nucleic acid was 1000 ng/μL. The total RNA was subjected to agarose gel electrophoresis, and it was confirmed that about 14.7 kb of double-stranded RNA (endornavirus genomic double-stranded RNA) was contained. The amount of the double-stranded RNA was about 0.058% (w/w) of the total nucleic acid.

Comparative Example 1: Total RNA Purified from Green Pepper (*Capsicum annuum* L. 'Grossum', Miogi)

Total RNA was purified from a green pepper (cultivar name: Miogi), for which it was known that the cells thereof do not contain endornavirus genomic double-stranded RNA, in the same manner as in Example 1.

Example 2: In Vitro Immunostimulatory Factor Production Test 1

Lung fibroblasts were obtained from 6-week-old C57BL/6J female mice, and cultured on a 6-cm dish by a general method for 3 days. Thereafter, the cells were seeded in a 12-well plate at 1×10³ cells/well, and cultured overnight. 50 μL/dish of the total RNA aqueous solution (nucleic acid: 1000 ng/μL) of Example 1 or Comparative Example 1, or water was added to this medium, and culturing was performed for 24 hours. After culturing, the mRNA expression levels of interferon-stimulated genes (ISG56 and CXCL10) were measured by quantitative RT-PCR. FIG. 1 shows the results.

As shown in FIG. 1, the green pepper-derived endornavirus genomic double-stranded RNA (Example 1) increased interferon-stimulated gene expression.

Example 3: In Vivo Immunostimulatory Factor Production Test 1

Figure 2:
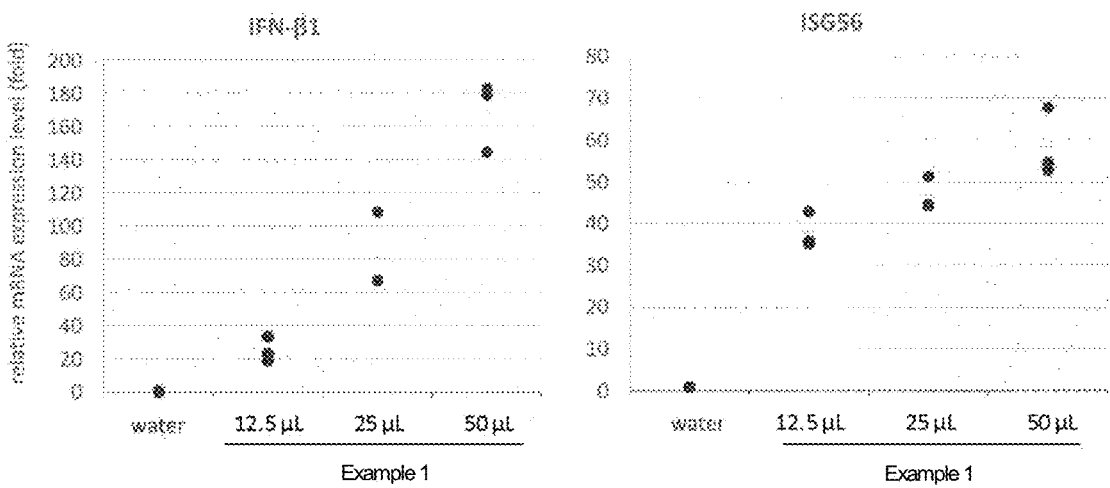
FIG. 2 shows the results of the in vivo immunostimulatory factor production test 1 of Example 3. The vertical axis represents relative expression levels.

6-week-old C57BL/6J female mice (n=3) were anesthetized by intraperitoneal injection of 15 μL of pentobarbital sodium prepared to 100 mg/ml with RNase-free water and diluted with 500 μL of PBS(=1.5 mg/body). The total RNA aqueous solution (nucleic acid: 1000 ng/μL) of Example 1 was intranasally administered (12.5 μL, 25 μL, or 50 μL/body). After administration, the nose of each mouse was flicked with a finger, and the mouse was laid face up, so that the administration sample reliably reached the lungs. Lungs were excised 24 hours after administration, and the mRNA expression levels of interferon (IFN-β1) and interferon-stimulated gene (ISG56) in the lungs were measured by quantitative RT-PCR. FIG. 2 shows the results.

As shown in FIG. 2, the green pepper-derived endornavirus genomic double-stranded RNA (Example 1) increased interferon expression and interferon-stimulated gene expression in a concentration-dependent manner.

Example 4: In Vivo Immunostimulatory Factor Production Test 2

Figure 3:
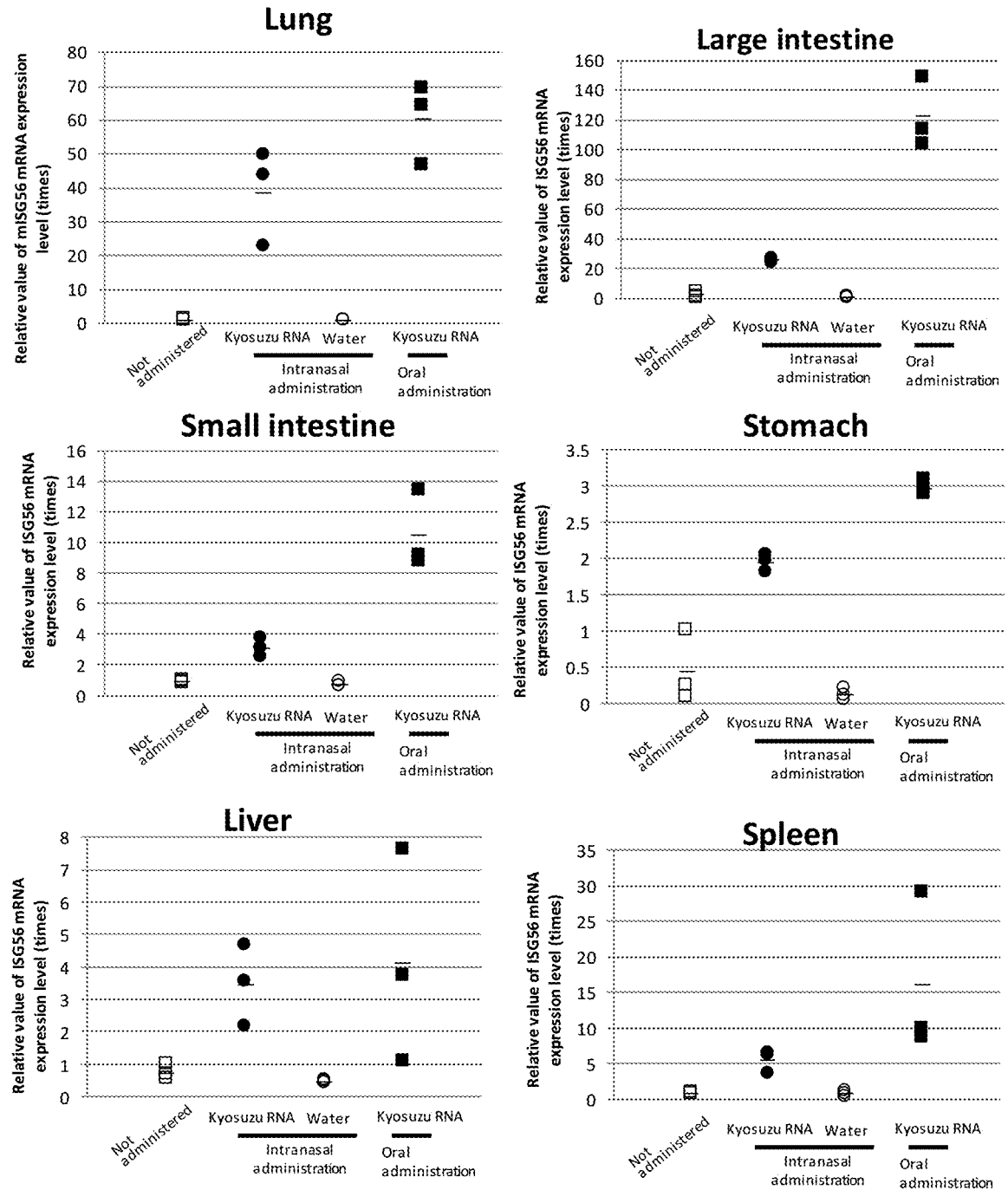
FIG. 3 shows the results of the in vivo immunostimulatory factor production test 2 of Example 4. The vertical axis represents relative expression levels. "Kyosuzu RNA" represents the total RNA obtained in Example 1.

The total RNA aqueous solution of Example 1 was intranasally administered (50 μL/body) to 6-week-old C57BL/6J female mice (n=3) in the same manner as in Example 3. In contrast, the total RNA aqueous solution of Example 1 was administered in the same manner as in Example 3, except that it was orally administered (300 μL/body) to 6-week-old C57BL/6J female mice (n=3). Twenty-four hours after administration, their organs (lungs, large intestine, small intestine, stomach, liver, and spleen) were excised, and the mRNA expression level of interferon-stimulated gene (ISG56) in each organ was measured by quantitative RT-PCR. FIG. 3 shows the results.

As shown in FIG. 3, the green pepper-derived endornavirus genomic double-stranded RNA (Example 1) increased interferon-stimulated gene expression in each tissue.

Example 5: Virus Infection Test 1 (Intranasal Administration)

Figure 4:
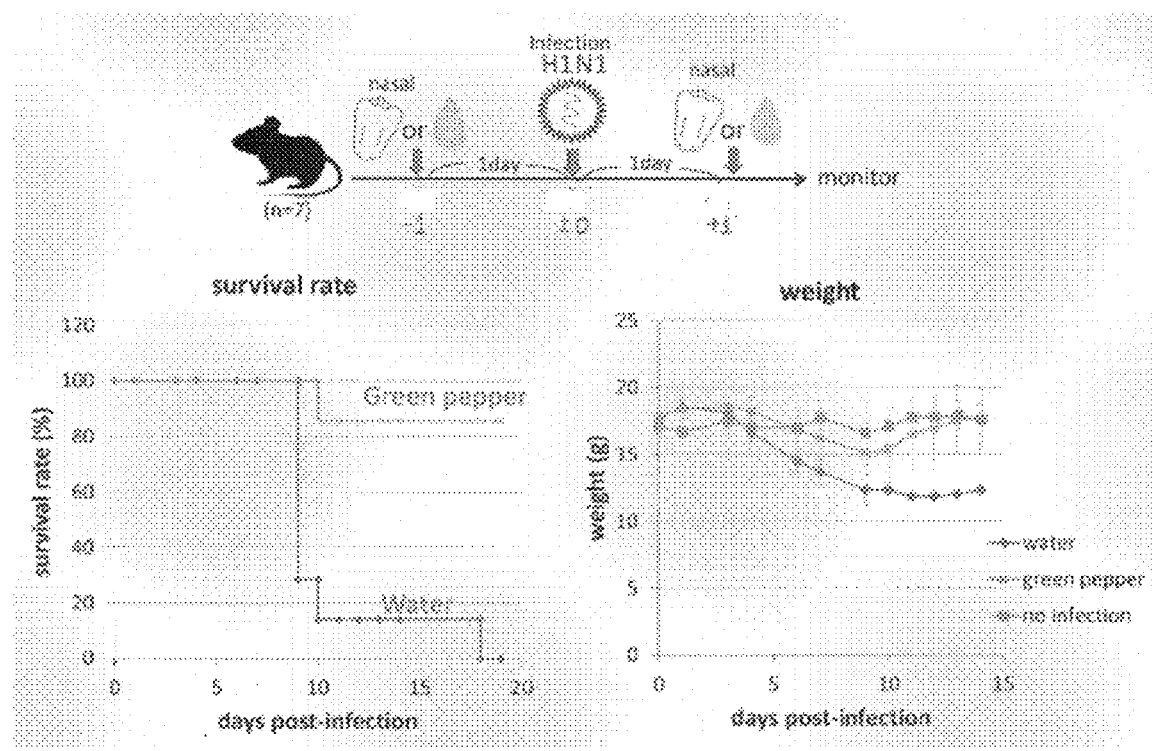
FIG. 4 shows the results of the virus infection test 1 of Example 5. The vertical axis of the left drawing represents survival rate, and the vertical axis of the right drawing represents body weight. The horizontal axis represents the number of days after infection. "Green pepper" represents a case of administering the total RNA obtained in Example 1.

The total RNA aqueous solution of Example 1 was intranasally administered (30 μL/body) to 6-week-old C57BL/6J female mice (n=7) in the same manner as in Example 3. One day after administration, 1.3×10⁷ pfu/μL× 50 μL/body of influenza A virus (H1N1) was infected by intranasal administration. One day after infection, the total RNA aqueous solution of Example 1 was intranasally administered (30 μL/body) in the same manner as in Example 3. The survival rate of the mice and their body weight were measured for a certain period of time after infection. FIG. 4 shows the results.

As shown in FIG. 4, the green pepper-derived endornavirus genomic double-stranded RNA (Example 1) suppressed survival rate reduction and weight loss caused by influenza A virus infection.

Example 6: Virus Infection Test 2 (Intranasal Administration)

Figure 5:
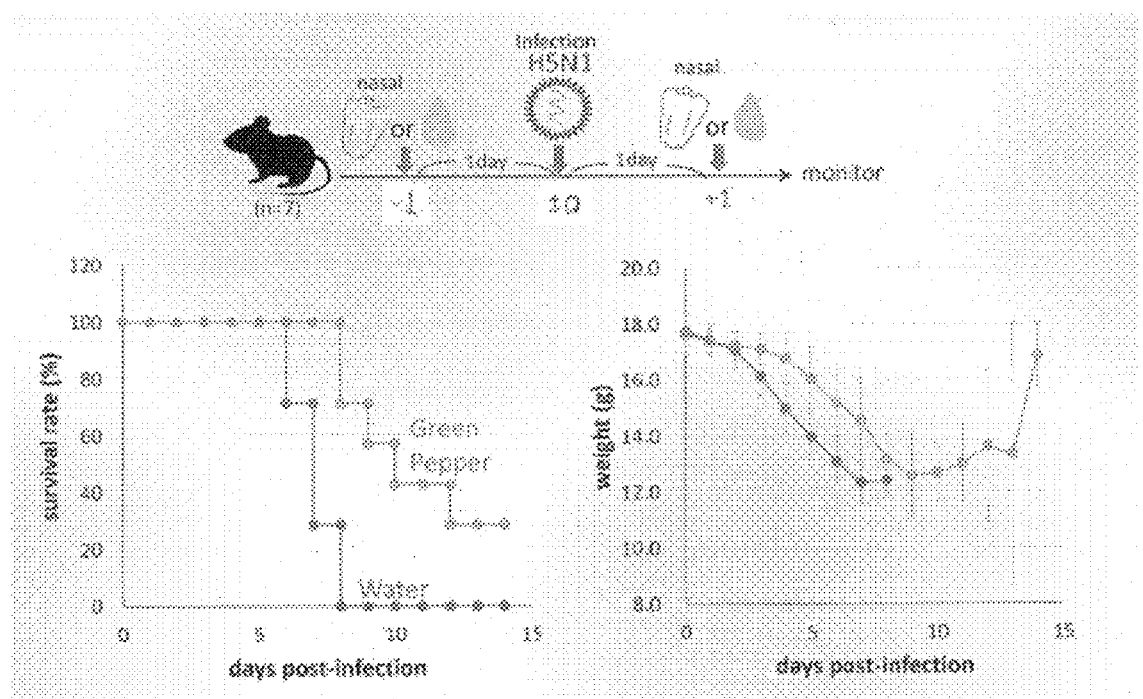
FIG. 5 shows the results of the virus infection test 2 of Example 6. The vertical axis of the left drawing represents survival rate. In the right drawing, the vertical axis represents body weight, and the horizontal axis represents the number of days after infection. "Green pepper" represents a case of administering the total RNA obtained in Example 1.
Figure 6:
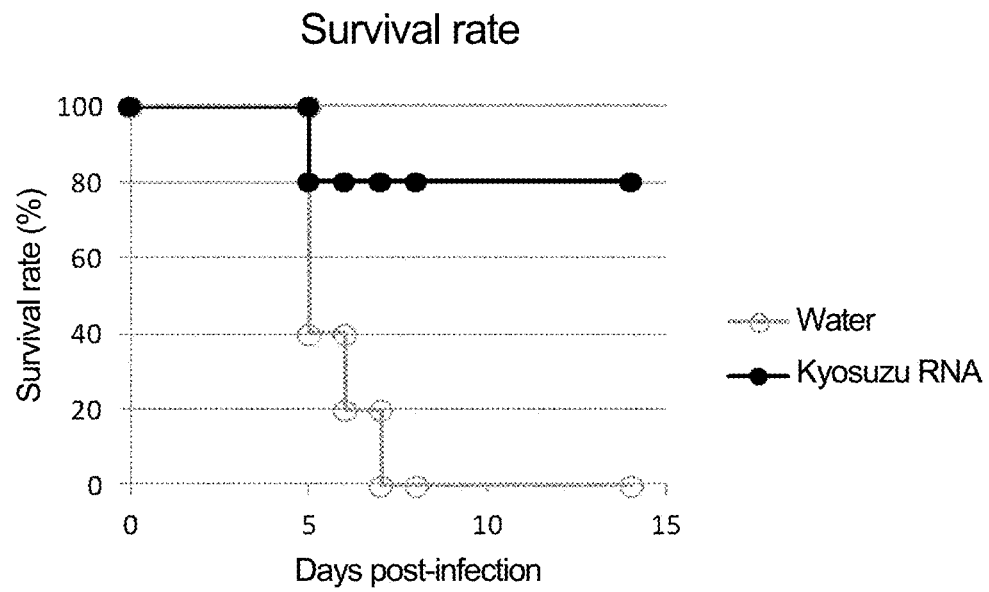
FIG. 6 shows the results of the virus infection test 3 of Example 7. The vertical axis represents survival rate. The horizontal axis represents the number of days after infection. "Kyosuzu RNA" represents the total RNA obtained in Example 1.
Figure 7:
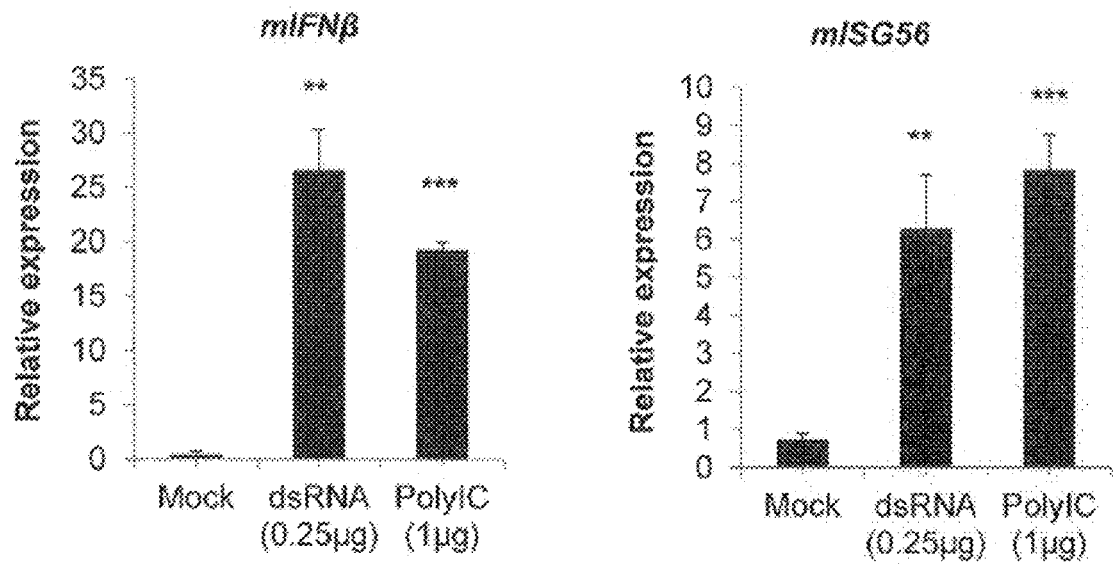
FIG. 7 shows the results of the in vitro immunostimulatory factor production test 2 of Example 10. The vertical axis represents relative expression levels. "dsRNA" represents the total RNA obtained in Example 8.
Figure 8:
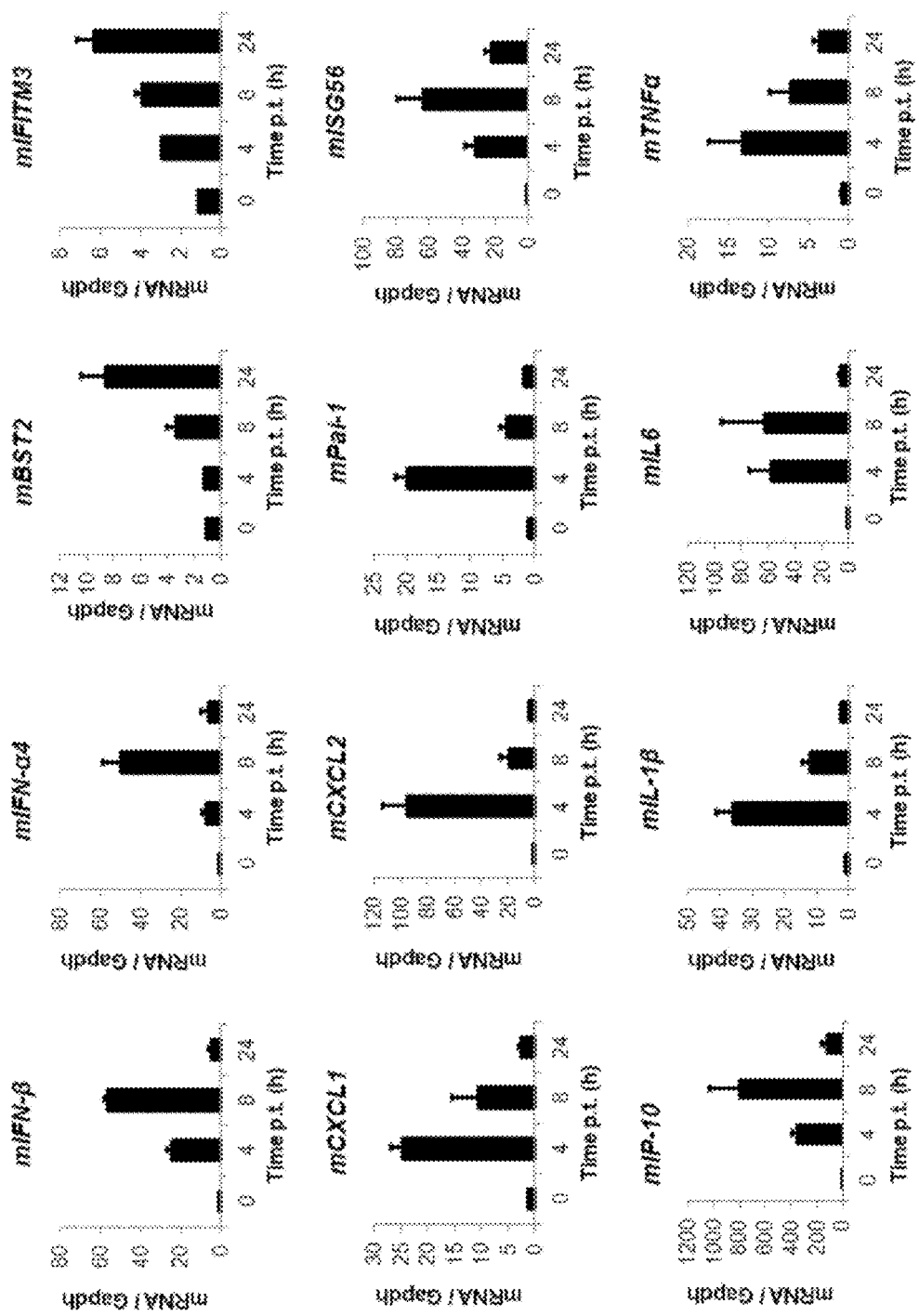
FIG. 8 shows the results of the in vivo immunostimulatory factor production test 3 of Example 11. The vertical axis represents relative expression levels, and the horizontal axis represents the time after administration.

The test was carried out in the same manner as in Example 5, except that highly virulent influenza A virus (H5N1) was used as the virus to infect. FIG. 5 shows the results.

As shown in FIG. 5, the green pepper-derived endornavirus genomic double-stranded RNA (Example 1) suppressed survival rate reduction and weight loss caused by highly virulent influenza A virus infection.

Example 7: Virus Infection Test 3 (Oral Administration)

The total RNA aqueous solution of Example 1 was orally administered (300 μL/body) to 6-week-old C57BL/6J female mice in the afternoon on the day (Day −1) just before the day of virus infection. In the morning of the next day (Day 0), $3.2\times10^7$ pfu/head (200 μL) of encephalomyocarditis virus (EMCV) was infected by oral administration. In the afternoon of the infection day (Day 0) and on the day (Day 1) following the infection day, the total RNA aqueous solution of Example 1 was orally administered (300 μL/body). The survival rate of the mice was measured for a certain period of time after infection. FIG. 6 shows the results.

As shown in FIG. 6, the green pepper-derived endornavirus genomic double-stranded RNA (Example 1) suppressed survival rate reduction caused by encephalomyocarditis virus infection.

Example 8: Double-Stranded RNA Purified from Rice Bran (*Oryza sativa*, Koshihikari (Cultivar))

Double-stranded RNA was purified from bran of rice (Koshihikari), for which it was known that the cells thereof contain endornavirus genomic double-stranded RNA. The specific operation was as follows.

After 300 mL of 0.5% DOC buffer (composition: 285 ml of 5 M NaCl and 3 M NaOAc (pH 5.2)+15 ml of 10% sodium deoxycholate (DOC)) was added and mixed with 60 g of rice bran of Koshihikari (cultivar), the mixture was centrifuged (4° C., 10000 rpm, 15 minutes), and the supernatant was collected. An equivalent amount of phenol was added to the supernatant, followed by vigorous stirring. Then, the mixture was centrifuged (4° C., 8000 rpm, 10 minutes), and the supernatant was collected. This phenol extraction operation was repeated twice. An equivalent amount of phenol/chloroform solution was added to the supernatant, followed by vigorous stirring. Then, the mixture was centrifuged (4° C., 3500 rpm, 3 minutes), and the supernatant was collected. After an equivalent amount of isopropanol was added to the supernatant and stirred, the mixture was centrifuged (4° C., 10000 rpm, 30 minutes), and the supernatant was removed. The precipitate was washed with 70% aqueous ethanol solution, and dissolved in 10 mM TE buffer. After lithium chloride was added and mixed with the obtained solution so that the final concentration was 2.25 M, the mixture was allowed to stand on ice for 2 hours, and then centrifuged (4° C., 15000 rpm, 15 minutes), and the supernatant was collected. After lithium chloride was added and mixed with the supernatant so that the final concentration was 4 M, the mixture was allowed to stand on ice for 2 hours, and then centrifuged (4° C., 15000 rpm, 35 minutes).

The supernatant was removed to thereby obtain RNA. The RNA was subjected to agarose gel electrophoresis, and it was confirmed that about 14 kb of double-stranded RNA (endornavirus genomic double-stranded RNA) was contained.

Example 9: Double-Stranded RNA Purified from Rice Bran (*Oryza sativa*, Koshihikari (Cultivar))

After 15 mL of 0.5% DOC buffer was added and mixed with 60 g of rice bran of Koshihikari (cultivar), the mixture was centrifuged (4° C., 10000 rpm, 15 minutes), and the supernatant was collected. Sodium chloride was added to the supernatant so that the final concentration was 1.6 M. Further, PEG #6000 was added so that the final concentration was 6.5%. After stirring, the resultant was allowed to stand on ice for 2 hours, and then centrifuged (4° C., 10000 rpm, 60 minutes), and the supernatant was removed. The precipitate was washed twice with 70% aqueous ethanol solution, air-dried, and then dissolved in 5 mL TE buffer. After an equivalent amount of phenol was added to the obtained solution and vigorously stirred, the mixture was centrifuged (4° C., 8000 rpm, 10 minutes), and the supernatant was collected. This phenol extraction operation was repeated twice. After an equivalent amount of chloroform was added to the supernatant and vigorously stirred, the mixture was centrifuged (4° C., 3500 rpm, 3 minutes), and the supernatant was collected. After an equivalent amount of isopropanol was added to the supernatant and stirred, the mixture was centrifuged (4° C., 10000 rpm, 30 minutes), and the supernatant was removed. The precipitate was dissolved in 1 mL ultrapure water, followed by gel filtration (Sepharose 4B), thereby purifying about 14 kb of double-stranded RNA.

Example 10: In Vitro Immunostimulatory Factor Production Test 2

Mouse embryonic fibroblasts were cultured in a 6-well plate dish by a general method. 1 μg of the RNA aqueous solution (containing 0.25 μg of double-stranded RNA) of Example 8 or PolyIC was added, together with lipofectamine (/dish), to the medium, and culturing was performed for 6 hours. After culturing, the mRNA expression levels of interferon (IFN-β1) and interferon-stimulated gene (ISG56) were measured by quantitative RT-PCR. FIG. 7 shows the results.

As shown in FIG. 7, the rice bran-derived endornavirus genomic double-stranded RNA (Example 8) increased interferon expression and interferon-stimulated gene expression.

Example 11: In Vivo Immunostimulatory Factor Production Test 3

The RNA aqueous solution of Example 8 (containing 20 μg of double-stranded RNA) was intranasally administered to 6-week-old C57BL/6J female mice in the same manner as in Example 3. Lungs were excised 0, 4, 8, and 24 hours after administration, and various mRNA expression levels were measured by quantitative RT-PCR. FIG. 8 shows the results.

It was shown that intranasal administration of the rice bran-derived endornavirus genomic double-stranded RNA (Example 8) could also promote the production of interferon (e.g., IFN-β1 and IFNα4), interferon-stimulated factors (e.g., ISG56, BST2, IFITM3, CXCL1, CXCL2, and Pai-1), and cytokines (e.g., IL-U, IL6, and INFα) in the lungs (FIG. 8).

Example 12: Virus Infection Test 4 (Intranasal Administration)

Figure 9:
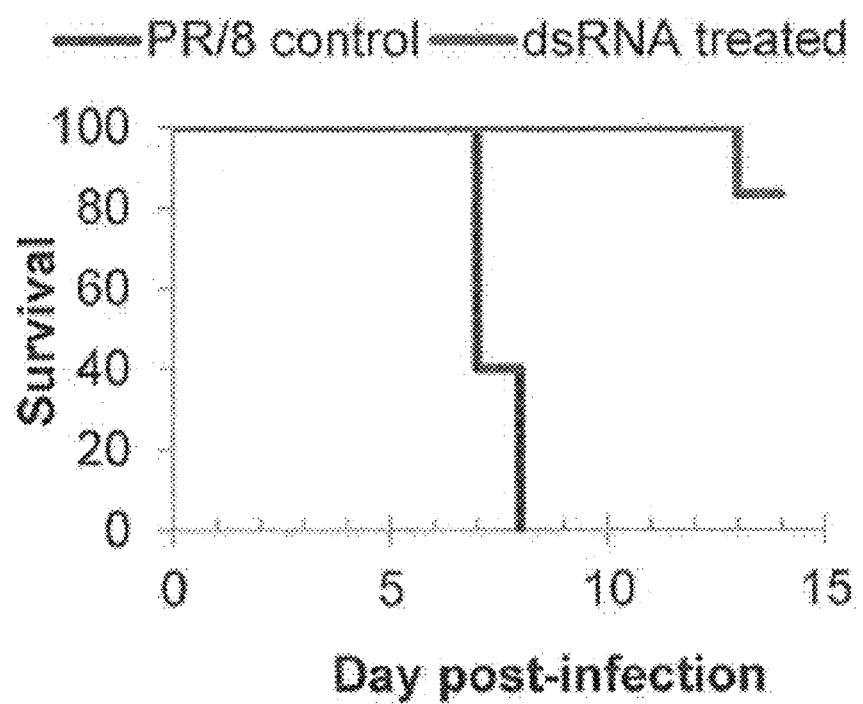
FIG. 9 shows the results of the virus infection test 4 of Example 12. The vertical axis represents survival rate, and the horizontal axis represents the number of days after infection. "dsRNA treated" represents a case of administering the RNA of Example 8, and "PR/8 control" represents a case of administering water in place of the RNA of Example 8.

The RNA aqueous solution (containing 20 µg of double-stranded RNA) of Example 8 was intranasally administered to 6-week-old C57BL/6J female mice (n=5) in the same manner as in Example 3. Eight hours after administration, influenza A virus (H1N1) was infected by intranasal administration in the same manner as in Example 3, and the RNA aqueous solution (containing 20 µg of double-stranded RNA) of Example 8 was intranasally administered in the same manner as in Example 3. The survival rate of the mice and their body weight were measured for a certain period of time after infection. FIG. 9 shows the results.

As shown in FIG. 9, the rice bran-derived endornavirus genomic double-stranded RNA (Example 8) suppressed survival rate reduction caused by influenza A virus infection.

Example 13: Virus Infection Test 5 (Intranasal Administration)

Figure 10:
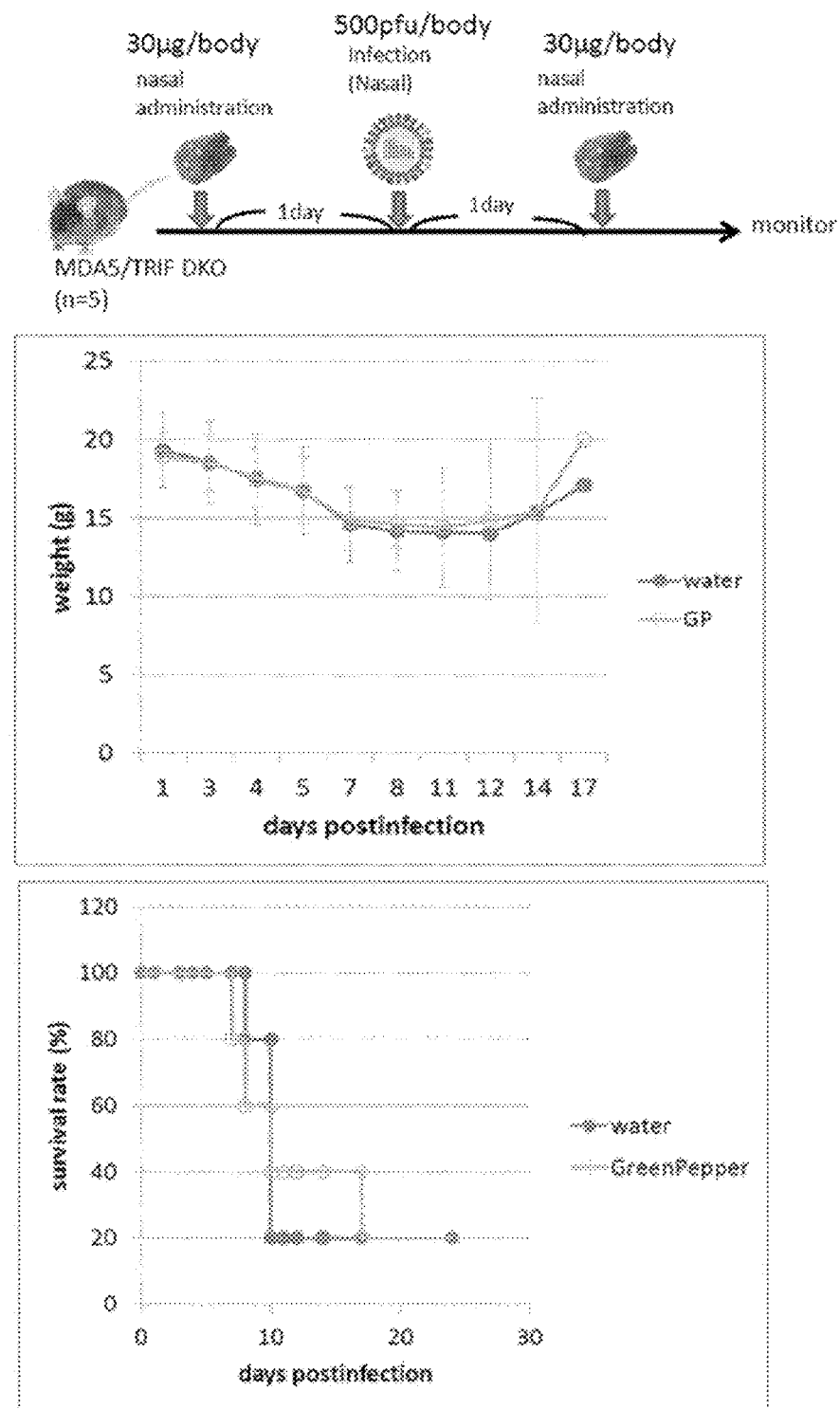
FIG. 10 shows the results of the virus infection test 5 of Example 13. The vertical axis of the upper drawing represents body weight, and the vertical axis of the lower drawing represents survival rate. The horizontal axis represents the number of days after infection. "GP" and "Green pepper" represent cases of administering the total RNA obtained in Example 1.

The test was carried out in the same manner as in Example 5, except that MAD5/TRIF double knockout mice (n=5) were used as the mice. FIG. 10 shows the results.

As shown in FIG. 10, in the MAD5/TRIF double knockout mice, survival rate reduction caused by influenza A virus infection was less suppressed than that by the green pepper-derived endornavirus genomic double-stranded RNA (Example 1). This suggested that the effect of the endornavirus genomic double-stranded RNA was an effect through signal-transduction pathways via MAD5 and/or TRIF.

Example 14: In Vivo Immunostimulatory Factor Production Test 4

Figure 11:
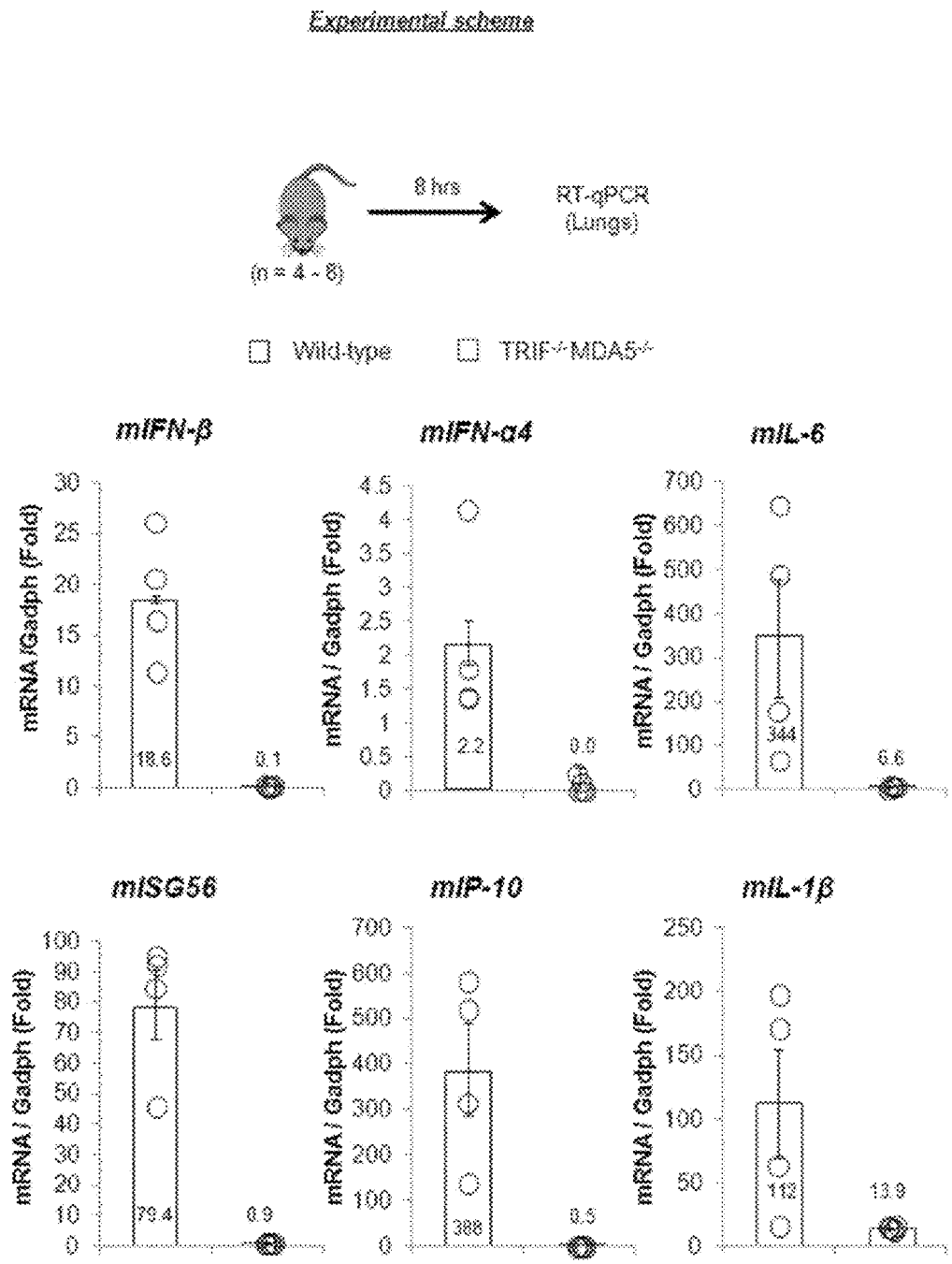
FIG. 11 shows the results of the in vivo immunostimulatory factor production test 4 of Example 14. The vertical axis represents relative expression levels. In each graph, the left column represents the results of wild-type mice, and the right column represents the results of MAD5/TRIF double knockout mice.

The test was carried out in the same manner as in Example 3, except that MAD5/TRIF double knockout mice (n=5) were used as the mice, and lungs were excised after 8 hours. FIG. 11 shows the results.

As shown in FIG. 11, increase in interferon expression and interferon-stimulated gene expression by the green pepper-derived endornavirus genomic double-stranded RNA (Example 1), which was observed in wild-type mice, did not occur in the MAD5/TRIF double knockout mice. This suggested that the effect of the endornavirus genomic double-stranded RNA was an effect through signal-transduction pathways via MAD5 and/or TRIF.

Example 15: Toxicity Test

Figure 12:
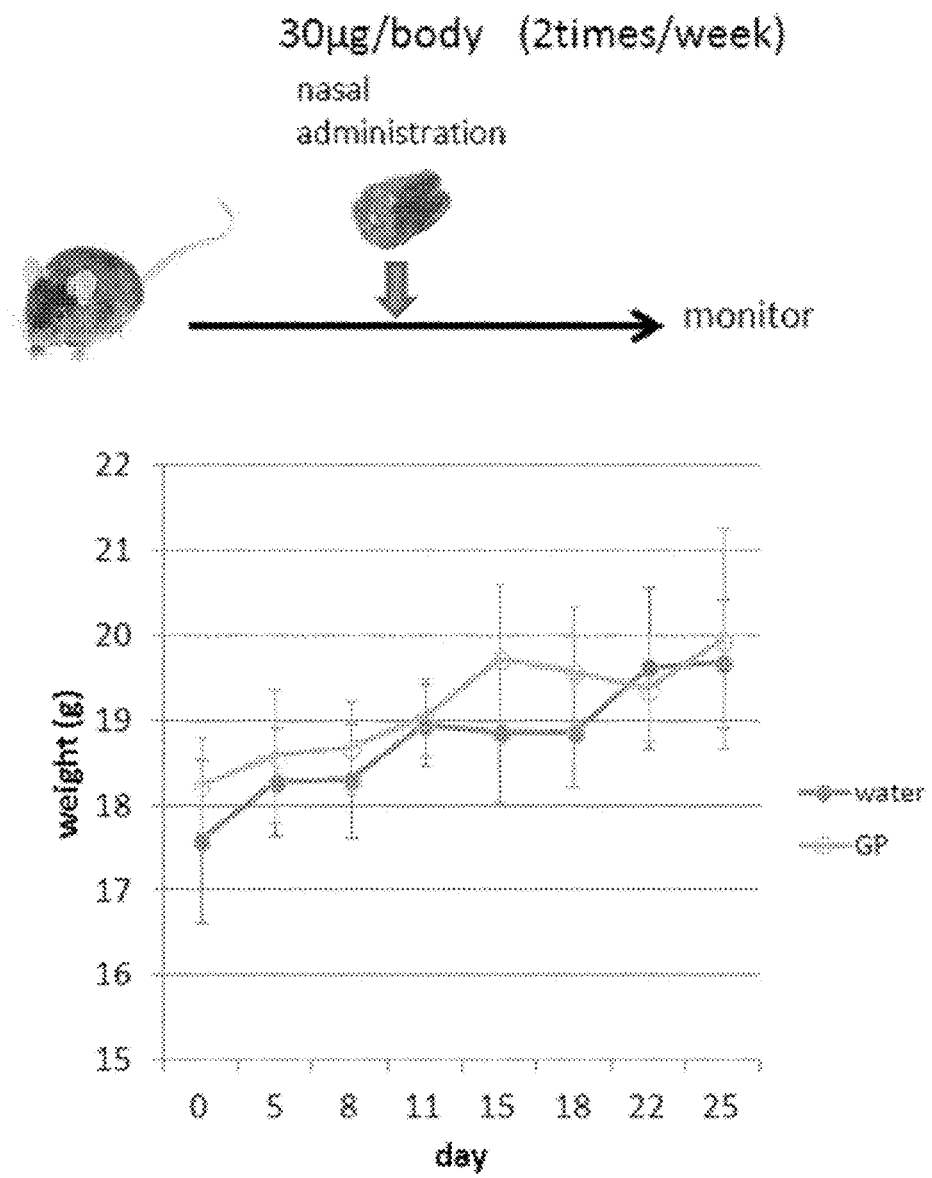
FIG. 12 shows the results of the toxicity test of Example 15. The vertical axis represents body weight, and the horizontal axis represents the number of days after the first administration.

The total RNA aqueous solution of Example 1 was intranasally administered (30 µL/body) to 6-week-old C57BL/6J female mice (n=5) in the same manner as in Example 3. This administration was continued twice a week, and changes in the body weight of the mice were measured. FIG. 12 shows the results.

As shown in FIG. 12, the body weight changes when the green pepper-derived endornavirus genomic double-stranded RNA (Example 1) was administered were equivalent to the body weight changes when water was administered.

Figure 13:
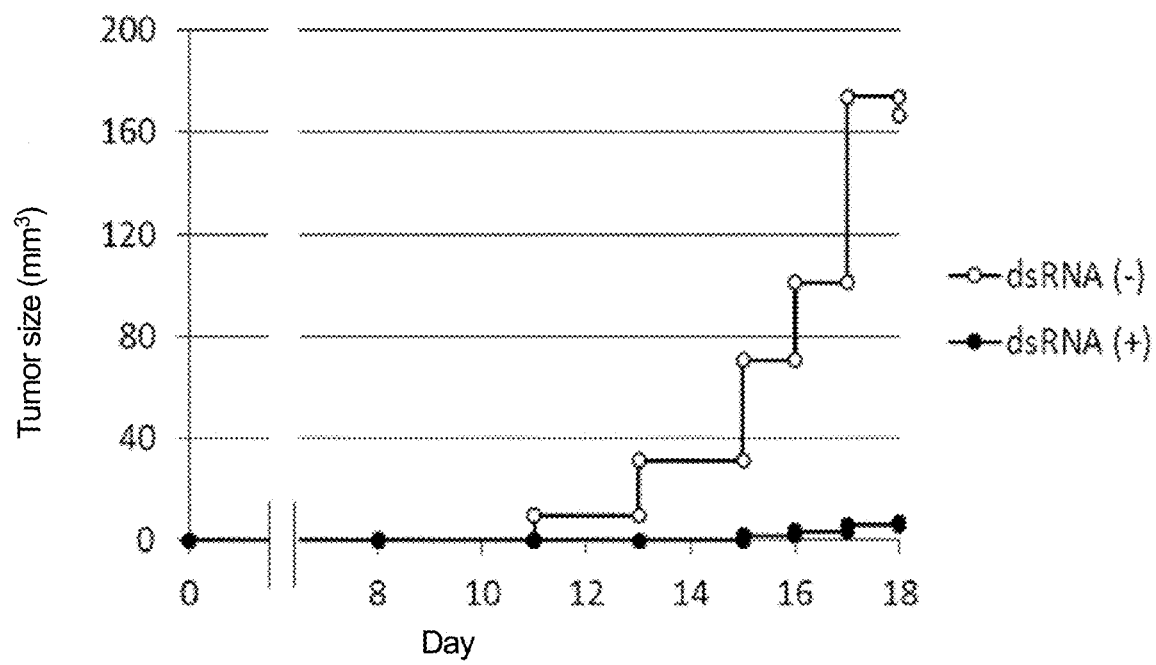
FIG. 13 shows the results of the evaluation test of cancer therapeutic and preventive effects of Example 16. The vertical axis represents tumor size, and the horizontal axis represents the number of days after subcutaneous injection of melanoma cells. "dsRNA (−)" represents a case of administering the total RNA of Comparative Example 1, and "dsRNA (+)" represents a case of administering the total RNA of Example 1.

Example 16: Evaluation Test of Cancer Therapeutic and Preventive Effects $1 \times 10^6$ melanoma cells (B16-F110 cells) were subcutaneously injected to 8-week-old C57BL/6J female mice (n=6 in each group; 12 in total). One day after subcutaneous injection, the total RNA aqueous solution of Example 1 containing 250 µg of double-stranded RNA was intraperitoneally administered twice a week. Tumor size was measured every day to every few days after subcutaneous injection. FIG. 13 shows the results.

As shown in FIG. 13, when the green pepper-derived endornavirus genomic double-stranded RNA (Example 1) was administered, tumor expansion could be almost completely suppressed.

Figure 14:
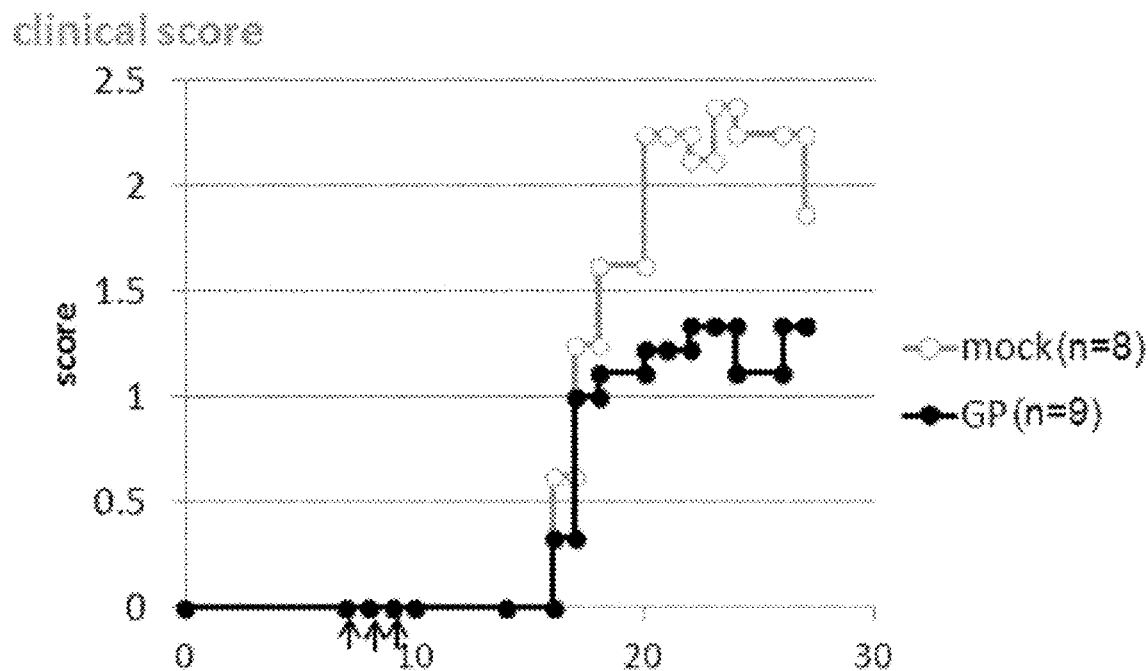
FIG. 14 shows the results of the evaluation test of multiple sclerosis therapeutic and preventive effects of Example 17. The vertical axis represents the clinical score of experimental autoimmune encephalomyelitis (EAE), which serves as a multiple sclerosis model, and the horizontal axis represents the number of days after administration of myelin oligodendrocyte glycoprotein (MOG) (day 0). "GP" represents a case of administering the total RNA obtained in Example 1.

Example 17: Evaluation Test of Multiple Sclerosis Therapeutic and Preventive Effects Myelin oligodendrocyte glycoprotein (MOG, 200 µg) and pertussis toxin (p-toxin, 0.5 µg) were administered to 8-week-old C57BL/6J female mice (n=17) (day 0). Two days (day 2) after MOG administration (day 0), pertussis toxin (p-toxin, 0.5 µg) was administered. As a result of these two administrations, EAE (experimental autoimmune encephalomyelitis) was induced as a multiple sclerosis model. The total RNA aqueous solution of Example 1 containing 30 µg of double-stranded RNA was intranasally administered to only nine of the entire mice (n=17) 7, 8, and 9 days (days 7, 8, and 9) after MOG administration (day 0). Clinical scores (0: normal (no symptom), 1: decreasing muscle tonus in tail, 2: complete paralysis in tail, 3: gait abnormality, and 4: hind-limb paralysis) were evaluated every day to every few days after MOG administration (day 0). FIG. 14 shows the results.

As shown in FIG. 14, when the green pepper-derived endornavirus genomic double-stranded RNA (Example 1) was administered, reduction in the EAE clinical scores could be suppressed.

Example 18: Double-Stranded RNA Purified from Rice Bran (*Oryza sativa*, Koshihikari (Cultivar))

After 2000 mL of 0.25% sodium cholate solution (composition: 0.1 M NaCl and 0.25% sodium cholate) was added and mixed with 200 g of rice bran of Koshihikari (cultivar), the mixture was centrifuged (4° C., 3500 rpm, 10 minutes) or allowed to stand at 4° C. After centrifugation or allowing to stand, the supernatant (opaque white and cloudy) was collected. ¼ volume of ethanol was added to the supernatant and stirred. The resulting mixture was allowed to stand on ice for 60 minutes, and then centrifuged (4° C., 3500 rpm, 20 minutes), and the supernatant was removed. 200 mL of RNA solubilization solution (composition: 0.1 M NaCl and a chelating agent (50 mM sodium citrate or 50 mM trisodium hydrogen ethylenediaminetetraacetate)) was added to the precipitate, and the precipitate was suspended. The suspension was centrifuged (4° C., 10000 rpm, 10 minutes), and the supernatant was collected. A double volume of ethanol was added to the supernatant and stirred. The resulting mixture was allowed to stand on ice for 60 minutes, and then centrifuged (4° C., 3500 rpm, 20 minutes), and the supernatant was removed. It was confirmed that the obtained precipitate contained endornavirus double-stranded RNA. The obtained precipitate was a viscous paste. This precipitate is pulverized by freeze drying or the like, whereby the endornavirus double-stranded RNA can be stored for a long period of time.

Example 19: In Vivo Immunostimulatory Factor Production Test 4

Figure 15:
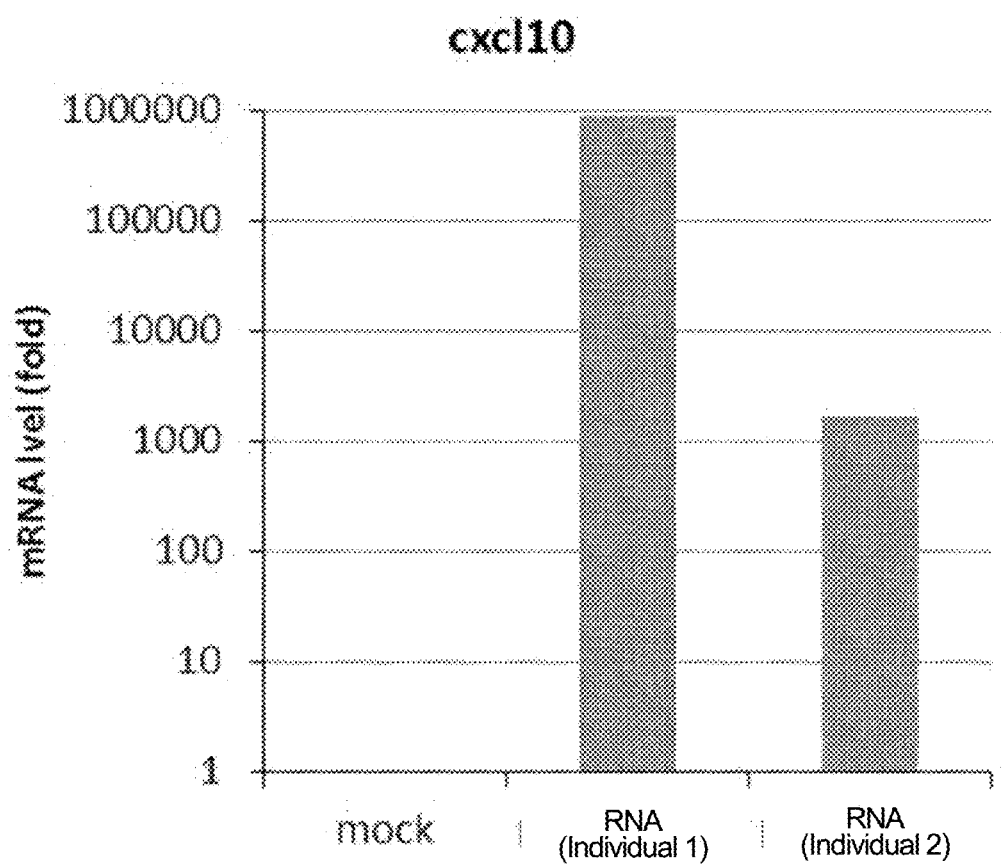
FIG. 15 shows the results of the in vivo immunostimulatory factor production test 4 of Example 19. The vertical axis represents relative expression levels. In the horizontal axis, "mock" represents a case of administering water, and "RNA (Individual 1)" and "RNA (Individual 2)" represent the results of administering the total RNA obtained in Example 1 to two micro mini pigs.

Micro mini pigs (5 kg) were anesthetized, and the total RNA aqueous solution (containing 4 mg of green pepper-derived RNA (total RNA)) of Example 1 was intranasally administered. Lungs were excised 24 hours after administration, and the mRNA expression level of interferon-induced gene (Cxcl10) in the lungs was measured by quantitative RT-PCR. FIG. 15 shows the results. In FIG. 15, "RNA (Individual 1)" and "RNA (Individual 2)" represent the results of the two micro mini pigs.

As shown in FIG. 15, the green pepper-derived endornavirus genomic double-stranded RNA (Example 1) increased interferon-induced gene expression.

The invention claimed is:

1. A method for promoting immunostimulatory factor production in an animal or human, comprising administering a composition comprising a genomic double-stranded RNA of a plant-derived endornavirus to the animal or human.

2. The method according to claim 1, wherein the plant is a *capsicum* plant, a rice plant, or a *Vicia* plant.

3. The method according to claim 1, wherein the genomic double-stranded RNA has a length of 8 to 20 kbp.

4. The method according to claim 1, wherein the genomic double-stranded RNA is linear.

5. The method according to claim 1, wherein the composition is a pharmaceutical composition.

6. The method according to claim 1, wherein the composition is an intranasal preparation.

7. The method according to claim 1, wherein the composition is an oral preparation.

8. The method according to claim 1, wherein the composition is a food composition.

9. The method according to claim 1, wherein the animal or human has a viral infection.

10. The method according to claim 9, wherein the animal or human has an RNA viral infection.

11. The method according to claim 1, wherein the composition is used as an adjuvant.

12. The method according to claim 1, wherein the animal or human has cancer.

13. The method according to claim 1, wherein the plant is *Capsicum annuum* Kyousuzu.

14. The method according to claim 1, wherein the plant is *Oryza sativa* Koshihikari.

* * * * *